United States Patent [19]
Nichols

[11] Patent Number: 5,562,630
[45] Date of Patent: Oct. 8, 1996

[54] APPARATUS AND METHOD FOR INSERTION OF BLOOD VESSEL CATHETERS WITHOUT BLOOD LOSS

[76] Inventor: Charlotte A. Nichols, 1145 N. Main, Las Cruces, N.M. 88001

[21] Appl. No.: 374,345

[22] Filed: Jan. 18, 1995

[51] Int. Cl.$^6$ ................................................ A61M 5/178
[52] U.S. Cl. ........................................... 604/164; 604/283
[58] Field of Search ............................ 604/283, 164–170, 604/264

[56] References Cited

U.S. PATENT DOCUMENTS

| | | | |
|---|---|---|---|
| 4,772,266 | 9/1988 | Groshong | 604/164 |
| 5,026,351 | 6/1991 | Dizon | 604/164 |
| 5,149,324 | 9/1992 | Clawson | 604/164 X |
| 5,201,712 | 4/1993 | Bryant | 604/164 |
| 5,215,528 | 6/1993 | Purdy et al. | 604/164 |
| 5,279,570 | 1/1994 | Dombrowski et al. | 604/264 X |

*Primary Examiner*—John D. Yasko
*Attorney, Agent, or Firm*—Deborah A. Peacock; Donovan F. Duggan

[57] ABSTRACT

The invention is to be used in conjunction with other medical devices that are designed to be attached to catheters. The use of the placement needle through the other components prevents the spillage of blood that usually occurs when catheters are inserted into blood vessels by acting as a sturdy guide for the pliable catheter tip and shaft while passing through a seal before penetrating a blood vessel. The catheter is pushed inside the vessel while the needle is removed and discarded. After the placement needle is removed from the unit blood fills the chambers but is trapped by the seal at the end of the injection site.

Also disclosed is a method of using the invention.

9 Claims, 1 Drawing Sheet

APPARATUS AND METHOD FOR INSERTION OF BLOOD VESSEL CATHETERS WITHOUT BLOOD LOSS

BACKGROUND OF THE INVENTION

1. Field of the Invention (Technical Field)

This invention is a medical instrument specifically to be used while inserting catheters into the lumen of blood vessels without blood loss; and a method of using the invention.

2. Background Art

Catheters are inserted into the lumens of blood vessels (e.g., arteries, veins, etc.) of patients undergoing medical treatment. The process is clumsy, partly because the needles used to guide a pliable plastic catheter into the blood vessel must be removed before any other devices or tubing can be attached to it. Blood spillage nearly always occurs before the other devices and tubings can be attached because very few medical personnel acquire the skill and dexterity that is required to slow the flow of blood from the blood vessel through the catheter. Currently, the flow of blood coming from the blood vessel is not interrupted in any way and often spills outside the body before any other device that might stop the hemorrhage can be connected.

The system at this time, is "open," meaning that it allows blood to flow outward, and foreign particles to enter. This spillage of blood and possibility of contamination has many disadvantages: medical personnel are exposed to diseases that are carried through the bloodstream (e.g., HIV, hepatitis) each time they come in contact with the blood of another person; and patients see that their blood is flowing from their body and consider this situation distasteful. Some patients become frightened at the sight of the blood and react sometimes by jerking in a manner that dislodges the catheter. When this happens, the catheter must be replaced in another blood vessel at another location, causing a duplication of effort, time, and materials. Various supplies are needed to clean up the blood that has spilled. Cotton balls, alcohol swabs, large lap pads, gauze sponges, etc.; must be used to clean the patient and any soiled linens. These supplies become hazardous waste when tinged with blood and must be disposed of with further risk to personnel, using special treatment, and at extra expense to the medical facility. The catheter wings and other parts can become soiled when blood spillage occurs. The wings cannot be cleaned easily without taking a chance that the catheter will become dislodged. Any blood that is trapped under the wings creates an unsanitary condition if the wings are to be sutured to the skin through the hole in them that is provided for this purpose. Blood attracts bacteria, and infections can occur.

Currently there are also other disadvantages to using blood vessel catheters. The clumsiness of the procedure currently used invites opportunities for the various parts used to become contaminated during the procedure, increasing the patient's opportunities to become infected. The tubing used to administer intravenous fluids is inserted into the open of the catheter but it is not secured by any locking device. The tubing can easily be dislodged if pulled accidentally. When this happens, blood from the patient's body will flow freely from the vein, through the catheter, outside the body, sometimes in large amounts before the accident is discovered. If the catheter is to remain in place for a period of time, as is a frequent situation, additional devices must be secured to it to provide a "cap." This action requires time and is sometimes inconvenient as an order from a physician is required. Also required is the effort of locating the part and putting it into place. The separate action of screwing the injection site into place offers another opportunity for blood spilled, for contamination to occur, and another potential for personnel infection.

SUMMARY OF THE INVENTION

(Disclosure of the Invention)

An object of the invention is the provision of a tool that will eliminate the spillage of blood during the procedure of inserting catheters into the lumens of blood vessels;

Another object of the invention is the provision of an apparatus that can be used easily with other supplies and equipment already in place in most hospitals and health facilities;

Still another object of the invention is the protection of medical personnel from exposure to blood borne diseases (e.g., HIV and hepatitis);

Another advantage of the invention is the reduction of the amount of hazardous waste that is dangerous as well as expensive to dispose of;

Another advantage of the invention is the provision of a method of blood vessel catheter placement that is more comfortable:and less traumatic for patients to tolerate;

Still another advantage of the invention is the provision of an efficient method of inserting blood vessel catheters that is less clumsy and more efficient in terms of time and effort to complete the procedure;

Yet another advantage of the invention is the provision of a cleaner, more sanitary procedure that does not allow blood to accumulate on the catheter or other parts used;

Another advantage of the invention is the reduction of opportunities for infection of patients via contamination of any material parts used;

Yet another advantage of the invention is improvement of the procedure for inserting blood vessel catheters so that less response time is needed in emergency situations.

A final advantage of the present invention is the provision of apparatus so inexpensive and easy to manufacture that implementation can begin in a short period of time.

BRIEF DESCRIPTION OF THE DRAWINGS

FIG. 1-B shows another prior art catheter component (Interlink Injection site, patent pending, Baxter #2N3379), top view;

DESCRIPTION OF THE PREFERRED EMBODIMENT

(Best Mode for Carrying Out the Invention)

Figure 1A:
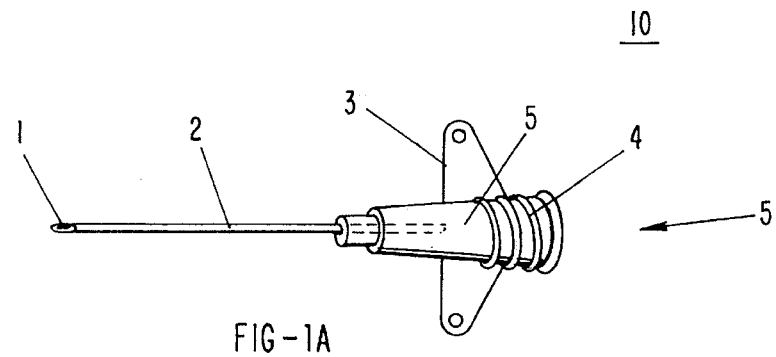
FIG. 1-A shows a prior art intravenous catheter (Insyte-W, Becton Dickinson Vascular Access), top view.
Figure 1B:
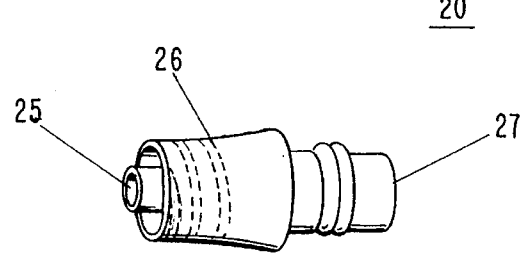

FIG. 1-A is the catheter portion 10 of an "Insyte-W" prior art intravenous catheter. Component 10 features a cylindrical, hollow, pliable, clear plastic tip 1 and shaft 2. Tip 1 and shaft 2 are inserted into blood vessels. The tip and shaft are attached to a plastic, hollow, open-ended, cone-shaped connection 5. The cone-shaped connection 5 is clear gray in color and features threads 4 and wings 3. The threads 4 match those of the "Interlink Injection Site," shown in FIG. 1-B. The holes in the wings 3 allow the catheter to be sutured into place if needed. The open-end of this part connects to any standard intravenous tubing by pushing the tubing into this end.

FIG. 1-B shows another prior art catheter component 20 known as an "Interlink Injection Site" (Baxter #2N3379, patent pending). Component 20 is cylindrical and has a hollow shaft 25 with an open end inside threaded portion 26. The hollow shaft 25 extends slightly past the end of the threaded portion 26. This shaft 25 leads into a larger chamber that is closed at the distal end by a rubber seal 27. Threads surround the base of the rubber seal 27. Component 20 is made of clear, sturdy plastic, except for the sealed end, which is made of rubber 27. The threads located near the open shaft 26 can connect this part to the intravenous catheter shown in FIG. 1-A because they match the threads 4. Other intravenous tubing and devices can be attached to component 20 via the threads near the rubber seal 27.

Figure 2:
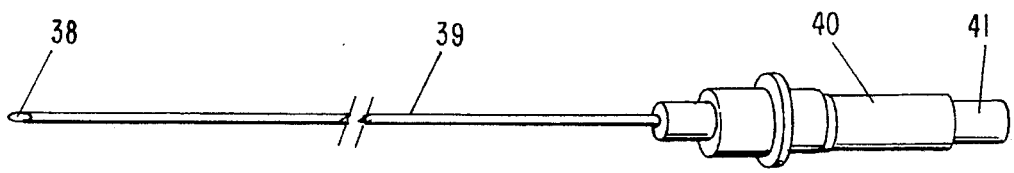
FIG. 2 shows the apparatus of the invention.

FIG. 2 shows the preferred apparatus of the present invention. Steel, hollow needle 39 allows for the passage of air and fluids through the unit. The distal end 38 features a beveled point. The needle 39 is attached to a clear plastic holder 40 that is rectangular in shape for ease of handling. The holder surrounds a hollow chamber and provides an open route from the beveled point 38 to the open end 41. The proximal end 41 is cylindrical and cone-shaped in form.

Figure 3:
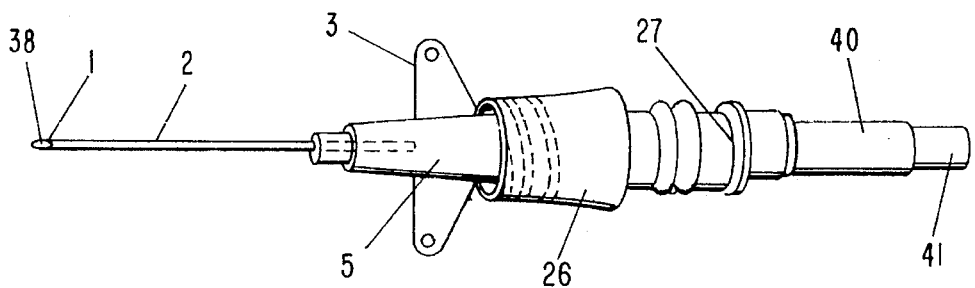
FIG. 3 shows the proper placement attachment and connection of the components depicted in FIGS. 1-A, 1-B, and 2.

FIG. 3 shows the proper placement and assembly of FIGS. 1, 2 and 3 connected to each other. Note that the beveled tip 38 of the needle 39 extends past the catheter tip 1. Also note that the components of FIG. 1-A and FIG. 1-B are screw-locked together, and that the needle 39 has been inserted through the rubber seal 27, into and through the pliable catheter shalt 2.

From the description above, a number of advantages of my patent become evident. The pieces are connected to each other prior to insertion into a blood vessel, eliminating the awkwardness and possible contamination of parts that occurs when trying to assemble the parts one at a time, as is the current procedure. Once inserted, blood will travel through the chambers in FIG. 1-A and 1-B, but will reach the rubber seal 27 and become trapped when the needle 39 is removed after insertion. The parts that remain adjacent to the body (FIGS. 1-A and 1-B) alter the procedure is completed are screw-locked together and will not easily be displaced or dislodged.

Any solutions to be attached will be connected to the "Interlink Injection Site" (FIG. 1-B) via the screwing threads near the rubber seal 27 and will be securely locked into place, safely and conveniently. These connections are not shown.

The manner of using the apparatus of the invention comprises attaching the intravenous catheter depicted in FIG. 1-A to the "Interlink Injection Site" depicted in FIG. 1-B by matching the screwing threads at 4 and 26 and twisting them clockwise, locking them together. After these two parts are connected, the tip of the needle 38 is passed into and through the rubber seal of the injection site 27, through the open shaft 25, through the pliable catheter 2, and slightly past the tip of the catheter 1. Its final position lies about ¼ inch past the catheter tip 1.

The properly connected unit as depicted in FIG. 3 is ready to insert into a blood vessel using standard medical procedures. The needle 39 acts a sturdy guide for the pliable catheter tip 1.

The tip of the needle 38 is used to pierce the skin and to enter a blood vessel below the skin. When a blood vessel is localized, blood will enter the needle and be seen as a red "flash" as it travels through the catheter tip 1 and shaft 2. At this point, the catheter is pushed, manually further into the vessel at the end of the shaft 2 as a separate motion, while the tip of the needle 38 remains behind it, but still in the catheter shaft 2.

After the catheter is inserted into the vessel as to cover shaft 2 and tip 1, the needle 30 is slowly pulled away from the unit, passing it back through the catheter and site component. The needle 30 passes the rubber seal 27 on its way out of the unit. The needle 30 is discarded and not used again.

While the needle 30 is being removed from the unit, blood from the vessel flows through the catheter (FIG. 2), and into the chamber near the rubber seal 27, but cannot flow any further after the needle 30 has been removed because it is trapped at the rubber seal 27. After the needle 30 is removed, the system is considered to be "closed" because no exchanges of blood, air, or particles can occur.

In contradistinction to the apparatus of my invention, the catheter depicted in FIG. 1-A is normally inserted with a shorter needle that is provided with it. After entry into a vessel is accomplished, the needle must be removed before any other devices or solutions can be attached. It is at this point, during the exchange of equipment, that the system is considered to be "open" because blood can flow freely from the vessel to areas outside the body. It is also at this point that contamination of the component parts is likely to occur, when medical personnel can become exposed to air airborne and blood borne diseases (e.g., HIV, hepatitis), that hazardous waste materials are created, when unsanitary conditions (e.g., blood on component parts) happen, and when foreign particles might enter the bloodstream. It is at this same time that personnel time is lost in having to clean up the blood spills created by the conventional procedures, that patients often become alarmed or frightened at the sight of their blood flowing freely and react in ways that sometimes dislodge the catheter which must then be replaced.

Although the description above contains many specificities, those should not be construed as limiting the scope of the invention but as merely providing illustrations of the presently preferred embodiments of the invention. For example, the needle can be increased in diameter and length to accommodate other blood vessel uses and devices (e.g., arterial line catheters) with minimal modifications. The sizes could be color-coded according to the length and gauge of the needle in order to prevent errors, etc. Thus, the scope of this invention should be determined by the appended claims and their equivalents rather than by the examples given.

I claim:

1. In combination:

a catheter comprising an elongated pliable tube at one end and a seal member at the other end;

a hollow catheter placement needle comprising a pointed beveled distal end and a chamber portion proximal end positioned within said catheter;

said pointed beveled distal end of said hollow catheter placement needle extending beyond the end of said elongated pliable tube; and said chamber portion of said hollow catheter placement needle is adjacent said seal member of said catheter.

2. The invention of claim 1 wherein said catheter placement needle comprises steel.

3. The invention of claim 1 wherein said chamber portion of said hollow catheter placement needle comprises clear plastic.

4. A catheter placement needle for use with a catheter member comprising a pliable tube at one end and a seal member at the other end, said needle comprising:

a hollow cylindrical body comprising a beveled point at a distal end; said hollow cylindrical body further comprising a hollow chamber portion at a proximal end; and said beveled point extending a predetermined distance beyond the end of a catheter tube tip of a catheter member while said hollow chamber portion is adjacent a seal member of the catheter member.

5. The invention of claim 4 wherein said hollow chamber portion comprises clear plastic.

6. The invention of claim 4 wherein said hollow chamber portion comprises a rectangular configuration.

7. The invention of claim 4 wherein said chamber portion of said hollow catheter placement needle means is rectangular in configuration.

8. A method of emplacing a catheter member comprising the steps of:

a) providing a catheter member comprising a pliable tube at one end and a seal member at the other end;

b) providing a catheter placement needle comprising a pointed beveled tip at a distal end and a hollow chamber portion at a proximal end; and c) inserting and extending the catheter placement needle through the seal member and beyond the tip of the pliable tube and thereafter positioning the seal member and the hollow chamber portion adjacent to each other.

9. The method of claim 3 further comprising the steps of:

a) puncturing a blood vessel with the distal end of the catheter placement needle;

b) inserting the catheter member into the blood vessel; and c) withdrawing the catheter placement needle.

* * * * *